(12) United States Patent
Van Dyke

(10) Patent No.: US 6,989,437 B2
(45) Date of Patent: Jan. 24, 2006

(54) METHODS FOR PRODUCING, FILMS COMPRISING, AND METHODS FOR USING HETEROGENEOUS CROSSLINKED PROTEIN NETWORKS

(75) Inventor: Mark E. Van Dyke, Fair Oaks Ranch, TX (US)

(73) Assignee: Keraplast Technologies, Ltd., San Antonio, TX (US)

( * ) Notice: Subject to any disclaimer, the term of this patent is extended or adjusted under 35 U.S.C. 154(b) by 442 days.

(21) Appl. No.: 10/133,885

(22) Filed: Apr. 26, 2002

(65) Prior Publication Data

US 2003/0204037 A1 Oct. 30, 2003

(51) Int. Cl.
*C07K 14/46* (2006.01)

(52) U.S. Cl. .................... 530/357; 514/12; 530/350; 530/356; 530/409; 530/410; 530/842

(58) Field of Classification Search ............... 514/12; 530/350, 356, 357, 409, 410, 842
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 2,434,688 A | 1/1948 | Evans | |
| 3,250,682 A | 5/1966 | Wilmsmann et al. | |
| 3,642,498 A | 2/1972 | Anker | |
| 3,677,693 A | 7/1972 | Fillingham | |
| 3,842,848 A | 10/1974 | Karjala | 424/71 |
| 4,041,150 A | 8/1977 | Karjala | 424/71 |
| 4,279,996 A | 7/1981 | Yoshioka et al. | 435/69 |
| 4,423,032 A | 12/1983 | Abe et al. | |
| 4,474,694 A | 10/1984 | Coco et al. | |
| 4,495,173 A | 1/1985 | Matsunaga et al. | |
| 4,504,644 A | 3/1985 | Lang et al. | |
| 4,570,629 A | 2/1986 | Widra | |
| 4,659,566 A | 4/1987 | Petrow | 424/71 |
| 4,751,074 A | 6/1988 | Matsunaga et al. | |
| 4,895,722 A | 1/1990 | Abe et al. | |
| 4,906,460 A | 3/1990 | Kim et al. | 424/70 |
| 4,959,213 A | 9/1990 | Brod et al. | 514/21 |
| 5,047,249 A | 9/1991 | Rothman et al. | |
| 5,073,294 A | 12/1991 | Shannon et al. | |
| 5,202,053 A | 4/1993 | Shannon | |
| 5,219,562 A | 6/1993 | Fujiu et al. | 424/71 |
| 5,243,028 A * | 9/1993 | O'Lenick, Jr. | 530/375 |
| 5,258,501 A | 11/1993 | Barbaric et al. | |
| 5,276,138 A | 1/1994 | Yamada et al. | |
| 5,300,285 A | 4/1994 | Halloran et al. | |
| 5,356,433 A | 10/1994 | Rowland et al. | |
| 5,358,935 A | 10/1994 | Smith et al. | 514/21 |
| 5,412,076 A | 5/1995 | Gagnieu | |
| 5,424,062 A | 6/1995 | Schwan et al. | 424/70.5 |
| 5,425,937 A | 6/1995 | Uchiwa et al. | 424/70.14 |
| 5,505,952 A | 4/1996 | Jiang et al. | |
| 5,520,925 A | 5/1996 | Maser | |
| 5,563,230 A | 10/1996 | Hsu et al. | |
| 5,654,471 A | 8/1997 | Zahn et al. | |
| 5,679,819 A | 10/1997 | Jones et al. | |
| 5,712,252 A | 1/1998 | Smith | |
| 5,833,880 A | 11/1998 | Siemensmeyer | |
| 5,932,552 A | 8/1999 | Blanchard et al. | |
| 5,942,009 A | 8/1999 | Burns | 8/432 |
| 5,948,432 A | 9/1999 | Timmons et al. | 424/443 |
| 5,955,549 A | 9/1999 | Chang et al. | |
| 5,989,461 A | 11/1999 | Coates et al. | |

(Continued)

FOREIGN PATENT DOCUMENTS

| | | |
|---|---|---|
| EP | 0097907 | 1/1984 |
| EP | 0 298 684 A3 | 1/1989 |
| EP | 0454 600 A1 | 10/1991 |
| EP | 0 468 797 A2 | 1/1992 |
| EP | 0 540 357 A2 * | 5/1993 |
| EP | 0540357 | 5/1993 |
| JP | 4-189833 | 7/1992 |
| JP | 2002-113815 | 4/2002 |
| WO | WO 93/10827 | 6/1993 |
| WO | WO 93/22397 | 11/1993 |
| WO | WO 98/08550 | 3/1998 |
| WO | WO 9931167 | 6/1999 |
| WO | WO 03008006 | 1/2003 |

OTHER PUBLICATIONS

S. F. Sadova and A. A. Konkin. Grafting of vinyl monomers onto wool keratin in an oxidation–reduction system. ZH Vses Khim O–va 1967; 12(5):596–7.

Iwata, et al.; Coating Film For Living Tissues; Nov. 2, 1985; total of 9 pages; Japanese Patent Application Kokai Publication No. Sho 60–220068.

Yoshioka et al; Modified Animal Hair or Wool Powder; Jul. 11, 1989; total of 13 pages; Japanese Unexamined Patent Application Publication H01–174528.

Miyamoto et al; Process for Producing Modified Keratin Protein; Feb. 6, 1982; total of 4 pages; Japanese Patent Application Kokai Publication No. Sho 57–23631.

Yamauchi et al; Keratin Microcapsule, Production of Keratin Microcapsule, and Cosmetics Containing Keratin Microcapsules; Dec. 22, 1998; total of 5 pages; Japanese Patent Application Kokai Publication No. H10–337466.

(Continued)

*Primary Examiner*—Robert A. Wax
(74) *Attorney, Agent, or Firm*—Vinson & Elkins L.L.P.

(57) ABSTRACT

Methods for producing biocompatible heterogeneous proteinaceous networks crosslinked with a heterogeneous crosslinking agent, and novel heterogeneous crosslinked networks. Preferred heterogeneous crosslinking agents are silicone-based.

26 Claims, No Drawings

U.S. PATENT DOCUMENTS

| | | | |
|---|---|---|---|
| 6,087,462 A | 7/2000 | Bowers et al. | |
| 6,090,308 A | 7/2000 | Coates et al. | |
| 6,110,487 A | 8/2000 | Timmons et al. | 424/443 |
| 6,124,265 A | 9/2000 | Timmons et al. | 424/443 |
| 6,159,495 A | 12/2000 | Timmons et al. | 424/443 |
| 6,159,496 A | 12/2000 | Blanchard | |
| 6,165,496 A | 12/2000 | Timmons et al. | 424/443 |
| 6,211,296 B1 | 4/2001 | Frate et al. | |
| 6,270,791 B1 | 8/2001 | Van Dyke et al. | 424/443 |
| 6,270,793 B1 | 8/2001 | Van Dyke et al. | 424/443 |
| 6,274,155 B1 | 8/2001 | Van Dyke et al. | 424/402 |
| 6,274,163 B1 | 8/2001 | Blanchard et al. | 424/443 |
| 6,316,598 B1 | 11/2001 | Van Dyke et al. | |
| 6,352,699 B1 | 3/2002 | Mondet et al. | |
| 6,358,501 B1 * | 3/2002 | Dietz et al. | 424/70.12 |
| 6,361,767 B1 | 3/2002 | Malle et al. | |
| 6,371,984 B1 | 4/2002 | Van Dyke et al. | |
| 6,379,690 B2 | 4/2002 | Blanchard et al. | |
| 6,399,051 B2 | 6/2002 | Dannecker et al. | |
| 6,432,435 B1 | 8/2002 | Timmons et al. | |
| 6,435,193 B1 | 8/2002 | Cannell et al. | |
| 6,461,628 B1 | 10/2002 | Blanchard et al. | |
| 6,565,842 B1 * | 5/2003 | Sojomihardjo et al. | 424/85.1 |

OTHER PUBLICATIONS

J.M. Gillespie, et al., "Amino Acid composition of a Sulphur–Rich Protein from Wool," Biochim. Biophy. Acta, (1960) pp. 538–539; vol. 39.

Keith H. Gough, et al., "Amino Acid Sequences of alpha – Helical Segments from S–Carboxymethylkerateine–A: Complete Sequence of a Type I Segment," Biochem. J. (1978), pp. 373–385; vol. 173.

Thomas C. Elleman, et al., "Amino Acid Sequences of alpha –Helical Segments from S–Carboxymethylkerateine–A:. Statistical Analysis," BIOCHEM. J. (1978), pp. 387–391, vol. 173.

David McC. Hogg, et al., "Amino Acid Sequences of alpha–Helical Segments from S–Carboxymethlkeratein–A:. Tryptic and Chymotryptic Peptides from a Type–II Segment," BIOCHEM. J. (1978), pp. 353–363; vol. 173.

W. Gordon Crewther, et al., "Amino Acid Sequences of alpha –Helical Segments from S–Carboxymethylkerateine–A: Complete Sequence of a Type–II Segment," BIOCHEM. J. (1978), pp. 365–371; vol. 173.

C. Earland, et al., "Studies on the Structure of Keratin: II. The Amino Acid Context of Fractions Isolated from Oxidized Wool," Biochemica et Biophysica Acta (1956), pp. 405–411, vol. 22.

J.M. Gillespie, et al., "Preparation of an Electrophoretically Homogeneous Keratin Derivative from Wool," Short Communications, Preliminary Notes, (1953), pp. 481–482, vol. 12.

Maurice J. Frenkel, et al., "The Isolation and Properties of a Tyrosine–Rich Protein from Wool: Component 0.62," Eur. J. Biochem, (1973) pp. 112–119, vol. 34.

R.J. Blagrove, et al., "The Electrophoresis of the High–Tyrosine Proteins of Keratins on Cellulose Acetate Strips," Comp. Biochem. Physiol., (1975) pp. 571–572, vol. 50B.

Robert C. Marshall, et al., "Successful Isoelectric Focusing of Wool Low–Sulphure Proteins," Journal of Chromatography, (1979) pp. 351–356, vol. 172.

Robert C. Marshall, "Characterization of the Proteins of Human Hair and Nail by Electrophoresis," The Journal of Investigation Dermatology, (1983) pp. 519–524, vol. 80.

W. G. Crewther, et al. "Helix–Rich Fraction from the Low–Sulphur Proteins of Wool," Nature, (Jul. 17, 1965) p. 295, No. 4994.

H. Lindley, et al., "Occurrence of the Cys–Cys Sequence in Keratins," J. Mol. Biol., (1967) pp. 63–67, vol. 30.

Robert C. Marshall, "Genetic Variation in the Proteins of Human Nail," The Journal of Investigative Dermatology, (1980) pp. 264–269, vol. 75.

M. E. Campbell, et al., "Compositional Studies of High–and Low–Crimp Wools," Aust. J. Biol. Sci., (1972) pp. 977–987, vol. 25.

P.J Reis, et al. "A Relationship between Sulphur Content of Wool and Wool Production by Merino Sheep," Aust. J. Biol. Sci., (1967) pp. 153–163, vol. 20.

Robert C. Marshall, et al., "The Keratin Proteins of Wool, Horn and Hoof from Sheep," Aust. J. Biol. Sci. (1977) pp. 389–400, vol. 30.

J.M. Gillespie. "Reaction of Sodium Borohydride with Wool," Nature, (Jan. 31, 1959) pp. 322–323, vol. 183.

David R. Goddard, et al., "A Study on Keratin," J. Bio. Chem., (1934) pp. 605–614, vol. 106.

L.M. Dowling, et al., "Isolation of Components from the Low–Sulphur Proteins of Wool by Fractional Preciptation Preparative Biochemistry," (1974) pp. 203–226, vol. 4 (3).

W.G. Crewther, et al., "Redution of S–Carboxymethylcysteine and Methionine with Sodium in Liquid Ammonia," Biochim. Biophys. Acta, (1969) pp. 609–611, vol. 164.

W.T. Agar, et al., "The Isolation from Wool of a Readily Extractable Protein of Low Sulphur Content," Biochim. Biophys Acta, (1958) pp. 225–226, vol. 27.

H. Lindley, et al., "The Reactivity of the Disulphide Bonds of Wool," Biochem J. (1974) pp. 515–523, vol. 139.

M. Schornig, et al., "Synthesis of Nerve Growth Fractor mRNA in Cultures of Developing Mouse Whisker Pad, A Peripheral Target Tissue of Sensory Trigeminal Neurons," The Journal of Cell Biology, (Mar. 1993) pp. 1471–1479, vol. 120, No. 6.

S. Mitsui, et al., "Genes for a Range of Growth Factors and Cyclin–Dependent Kinase Inhibitors are Expressed by Isolated Human Hair Follicles," British Journal of Dermatology (1997) pp. 693–698, vol. 137.

B.K. Filshie, et al., "The Fine Structure of alpha –Keratin," J. Mol. Biol. (1961) pp. 784–786, vol. 3.

R.D.B. Fraser, et al., "Structure of alpha –Keratin," Nature, (Feb. 28, 1959) pp. 592–594, vol. 183.

R.D.B. Fraser, et al. "Helical Models of Feather Keratin Structure," Nature, (Sep. 22, 1962) pp. 1167–1168, vol. 195.

B.K.Filshie, et al., "An Electron Microscope Study of the fine Structure of Feather Keratin," The Journal of Cell Biology (1962) pp. 1–12, vol. 13.

W.G. Crewther, et al., "Low–Sulfur Proteins from alpha – Keratins. Interrelationships between their Amino Acid Compositions, alpha–Helix Contents, and the Supercontraction of the Parent Keratin," Biopolymers (1966) pp. 905–916, vol. 4.

G.M. Bhatnagar, et al., "The Conformation of the High–Sulphur Proteins of Wool I. The Preparation and Properties of a Water–Sulphur Metakeratin," Int. J. Protein Research I. (1969), pp. 199–212.

W.G. Crewther, et al., "The Preparation and Properties of a Helix–Rich Fraction Obtained by Partial Proteolysis of Low Sulphur–Carboxymethlkerateine from Wool," (1967) The Journal of Biological Chemistry (Issue of Oct. 10), pp. 4310–4319, vol. 242, No. 19.

D.A.D. Parry, et al., "Structure of alpha –Keratin: Structural Implication of the Amino Acid Sequences of the Type I and II Chain Segments," J. Mol. Biol. (1977) pp. 449–454, vol. 113.

E. Suzuki, et al., "X–Ray Diffraction and Infrared Studies of an alpha –Helical Fragment from alpha –Keratin," J. MolL. Biol. (1973) pp. 275–278, vol. 73.

G.M. Bhatnagar, et al., "The Conformation of the High–Sulphur Proteins of Wool: II. Difference Spectra of Kerateine–B," Int. J. Research1, (1969) pp. 213–219.

Dean R. Hewish, et al., "In Vitro Growth and Differentiation of Epithelial Cells Derived from Post–Embroyonic Hair Follicles," Aust. J. Biol. Sci., (1982) pp. 103–109, vol. 35.

A.M. Downes, et al., "A Study of the Proteins of the Wool Follicle," Aust. J. Biol. Sci., (1966) pp. 319–333, vol. 19.

G. E. Rogers, et al., "Keratin Protofilaments and Riobsomes from Hair Follicles," Nature, (Jan. 2, 1965), pp. 77–78, vol. 205.

P.M. Steinert, et al., "In Vitro Studies on the Synthesis of Guinea Pig Hair Keratin Proteins," Biochimica et Biophysica Acta, (1973) pp. 403–412, vol. 312.

G.E. Rogers, et al., "Some Observations on the Proteins of the Inner Root Sheath Cells of Hair Follicles," Biochimica et Biophysica Acta, (1958) pp. 33–43, vol. 29.

Leslie N. Jones, et al., "Studies of Developing Human Hair Shaft Cells in Vitro," The Journal of Investigative Dermatology., (Jan. 1988) pp. 58–64, vol. 90.

Trevor Jarman, et al., "Prospects for Novel Biomaterials Development," Online Publications, Pinner, Uk, Presented at Biotech '85 (Europe) (1985) pp. 505–512.

Akira Tachibana, et al., "Fabrication of Wool Keratins Sponge Scaffolds for Long–Term Cells Cultivation," Journal of Biotechnology, (2002) pp. 165–170, vol. 93.

J.M. Gillispie, et al., "Periodicity in High–sulphur Proteins from Wool," Nature, (Sep. 18, 1965) pp. 530–531, vol. 246.

Kiyoshi Yamauchi, "The Development of Keratin: Characteristics of Polymer Films," [Research Report]; pp. 1–12.

"Scattering to Structural Foams, Skin, Synthetic" Encyclopedia of Polymer and Science and Engineering, (1989) pp. 335–345, vol. 15.

J.M. Gillespie, et al., "Proteins Rich in Glycine and Tyrosine from Keratins," Comp. Biochem. Physiol., (1972) pp. 723–734, vol. 41B.

R.D.B. Fraser, et al., "Tyrosine–Rich Proteins in Keratins," Comp. Biochem. Physiol., (1973) pp. 943–947, vol. 44B.

J.M. Gillespie, et al., "Relation Between the Tyrosine Content of Various Wools and their Content of a Class of Proteins Rich In Tyrosine and Glycine," Aust. J. Biol. Sci., (1971) pp. 1189–1197, vol. 24.

J.M. Gillespie, et al., "The Macroheterogeneity of Type I Tyrosine–rich Proteins of Merino Wool," Aust. J. Biol. Sci., (1974) pp. 617–627, vol. 27.

E.G. Bendit, et al., "The Probable Role and Location of High–Glycine–Tyrosine Proteins in the Structure of Keratins," BIOPOLYMERS, (1978) pp. 2743–2745, vol. 17.

Robert C. Marshall, et al. "High–sulphur Proteins from alpha –Keratins: II.* Isolation and Partial Characterization of Purified Components from Mouse Hair," Aust. J. Biol. Sci. (1976) pp. 11–20, vol. 29.

Robert C. Marshall, et al. "High–Sulphur Proteins from alpha –Keratins: 1. Heterogencity of the Proteins from Mouse Hair," Aust. J. Biol. Sci. (1976) pp. 1–10, vol. 29.

R. L. Darskus, et al. "The Possibility of Common Amino Acid Sequences in High–Sulphur Protein Fractions From Wool," Aust. J. Biol. Sci. (1969) pp. 1197–1204, vol. 22.

Robert C. Marshall, et al. "Heterogeneity and Incomplete Disulfide Reduction in the High–Sulphur Proteins of Wool," Aust. J. Biol. Sci. (1978) pp. 219–229, vol. 31.

H. Lindley, et al., "The Preparation and Properties of a Group of Proteins from the High– Sulphur Fraction of Wool," Biochem. J. (1972) pp. 859–867, vol. 128.

J.M. Gillespie, et al., "Evidence of Homology in a High–Sulphur Protein Fraction (SCMK–B2) of Wool and Hair alpha –Keratins," Biochem. J. (1968) pp. 193–198, vol. 110.

J.M. Gillespie, et al., "A Comparative Study of High–Sulphur Proteins from alpha–Keratins," Comp. Biochem. Physiol. (1965) pp. 175–185, vol. 15.

J.M. Gillespie, et al., "High–Sulphur Proteins as a Major Cause of Variation in Sulphur Content Between alpha –Keratins," Nature (Sep. 18, 1965) pp. 1293–1294, vol. 207.

R.D.B. Fraser, et al., "Molecular Organization in Alpha–Keratin," Nature, (Mar. 17, 1962) pp. 1052–1055, vol. 193.

Dr. P. Alexander, et al., "Structure of Wool Fibres," Nature, (Sep. 2, 1950) pp. 396–398.

Node, et al., "Hard Acid and Soft Nucleophile System. 2, Demethylation of Methyl Ethers of Alcohol and Phenol with an Aluminum Halide–Thiol System," J. Org. Chem (1980), pp. 4275–4277. vol. 45.

Ito, et al., "Biocompatibility of Denatured Wool Keratin," Konbushi Ronbunshu [Collected Essays on Polymers], (Apr. 1982) pp. 249–256, vol. 39, No. 4.

Tatsuya and Ishii, "Keratin Protein High Pressure Molded Article,"; Japanese Patent Application, (Dec. 3, 1993), total of six pages, Public Patent Announcement 1993–320358.

Saeki Yokogawa, and Uehara, "Production Method For Water–soluble Keratin Protein," Japanese Patent Application, (Feb. 21, 1990), total of five pages, Public Patent Announcement 1990–51533.

Miyamoto and Tsushima, "A Method for Preparing a Keratin Substance with a Low Molecular Weight," Japanese Patent Application (Jul. 8, 1982), total of five pages; Public Patent Disclosure Bulletin S57–109797.

R.D.B. Fraser, "The Chain Configuration of Wool Keratin," Short Communications, Preliminary Notes, (1953) pp. 482–483, vol. 12.

R.D.B. Fraser, et al., "Microscopic Observations of the Alkaline–Thioglycollate Extraction of Wool," Short Communications, Preliminary Notes, (1953) pp. 484, vol. 12.

Weetall HH.; Preparation of immobilized proteins covalently coupled through silane coupling agents to inorganic supports; Applied Biochemistry and Biotechnology; 1993; 157–188; 41(3).

Weethall, HH.; Preparation of immobilized proteins covalently coupled through silane coupling agents to inorganic supports; Advances in Molecular and Cell Biology; 1996; 161–192; 15A.

Van Dyke Mark et al., Development of keratin coatings for osteoinduction on titanium, ,Abstracts of Papers American Chemical Society, vol. 224, No. 1–2, 2002,Aug. 18–22, 2002.

Tanaka, Yoshio et al., Reaction of Wool Keratin with Epoxides, Proceedings International Wolitextil–Forschungskonf, vol. 3, 1976, pp. 192–201.

Fraenkel–Conrat, H., The Action of 1, 2–Exposides on Proteins, Journal of Biological Chemistry, vol. 154, No. 1, Jun. 1, 1944.

* cited by examiner

METHODS FOR PRODUCING, FILMS COMPRISING, AND METHODS FOR USING HETEROGENEOUS CROSSLINKED PROTEIN NETWORKS

CROSS-REFERENCE TO RELATED APPLICATIONS

The present application is related to the following pending applications: U.S. patent application Ser. No. 10/119,477, filed Apr. 10, 2002; and U.S. patent application Ser. No. 10/127,523, filed Apr. 22, 2002. The present application is also related to the following provisional applications: U.S. Provisional Application No. 60/200,543, filed Apr. 27, 2000; U.S. Provisional Application No. 60/225,517, filed Aug. 15, 2000; U.S. Provisional Application No. 60/324,709, filed Sep. 25, 2001; U.S. Provisional Application No. 60/393,958, filed Jul. 5, 2002; and U.S. Provisional Application No. 60/399,039, filed Jul. 25, 2002.

FIELD OF THE INVENTION

The present invention is directed to methods for producing biocompatible heterogeneous proteinaceous networks crosslinked with a heterogeneous crosslinking agent, preferably a silicone-based crosslinking agent. Preferred proteins for use in forming the networks are α-keratin, or high molecular weight keratin (HMWK's). The crosslinking agent preferably reacts with reactive pendant groups existing on the keratin molecules and either produces no byproducts, produces biocompatible byproducts, such as hydrogen, water, and carbon dioxide, or produces byproducts that can be removed from the network.

BACKGROUND OF THE INVENTION

Proteins, such as keratin proteins, are beneficial in healing damaged epithelial tissues. Unfortunately, the chemical and engineering properties of keratin proteins have been relatively limited to those achieved using oxidative and reductive chemistries, and side chain protein crosslinks. A need exists for proteins, and methods for crosslinking proteins, preferably α-keratin, to form films having a broad scope of chemical and engineering properties so that the potential applications of protein-based materials can be expanded.

SUMMARY OF THE INVENTION

A method is provided for making a keratin network interlinked by a silicone-based crosslinking agent, said method comprising exposing a plurality of α-keratin molecules comprising reactive pendant groups to a multifunctional silicone-based crosslinking agent under conditions effective to form covalent interprotein crosslinks between first reactive functionalities on said crosslinking agent and first reactive pendant groups on a first group of said α-keratin molecules, said conditions also being effective to form covalent interprotein crosslinks between second reactive functionalities on said crosslinking agent and second reactive pendant groups on a second group of α-keratin molecules.

Also provided are networks comprising proteinaceous material consisting essentially of α-keratin molecules comprising interprotein crosslinks comprising first covalent bonds between first reactive functionalities on a plurality of molecules of a silicone-based crosslinking agent and first reactive pendant groups on a plurality of first α-keratin molecules and second covalent bonds between second reactive functionalities on a plurality of molecules of said silicone-based crosslinking agent and second reactive pendant groups on a plurality of second α-keratin molecules.

DETAILED DESCRIPTION OF THE INVENTION

The present invention is directed toward methods for crosslinking proteins, preferably using heterogeneous crosslinking agents to form heterogeneous proteinaceous networks or films. As used herein, the term "heterogeneous" refers to a proteinaceous network or film, preferably comprising protein molecules having a relatively high molecular weight of at least about 50 kDa, preferably from about 50 to about 85 kDa, or derivatives therefrom. The protein molecules are interlinked by a silicone-based crosslinking material.

The methods described herein may be used to treat a wide variety of proteins to form network structures, preferably elastomeric films. Examples of suitable naturally occurring proteins include, but are not necessarily limited to keratin, collagen, and elastin. The proteins may be natural, synthetic, or recombinant. Preferred proteins are relatively high in cysteine content. Most preferred proteins are keratin proteins, even more preferably α-keratin proteins, also sometimes called high molecular weight keratin (HMWK's).

A preferred source of keratin proteins is hair or fur. The hair may be animal, or human. Keratin are loosely defined as the hardened and insolubilized proteins found in the epidermal cells of vertebrates. Human hair is composed almost entirely of keratin.

Human hair has a cuticle, which is a tough tubular outer layer made up of flattened cells arranged in a scaly, overlapping profile. The inner bulk of the hair is called the cortex and is constructed from elongated cells that are densely packed with fibrous keratin. The fibrous keratin are arranged in bundles referred to as microfibrils and possess an α-helical tertiary structure. The microfibrils are bound together with an amorphous keratin matrix.

The amorphous keratin matrix and the microfibrils vary in function and composition. The matrix is the "glue" that holds the microfibrils together. This matrix "glue" is high in sulfur content, and is comprised of low molecular weight keratin (LMWK) which typically have an average molecular weight of from about 10 to about 15 kDa. The microfibrils are comprised of high molecular weight keratin (HMWK) having a relatively lower sulfur content, but having a higher average molecular weight of typically from about 50 to about 85 kDa. HMWK's and LMWK's vary in chemical properties, such as reactivity and solubility.

Keratin are afforded their structural integrity, in large part, by the presence of disulfide crosslinks which form a three dimensional network of polypeptide chains. This network structure renders keratin insoluble. Keratin can, however, be made water soluble by destroying this three dimensional structure via disulfide bond scission. Disulfide bond scission can be performed either oxidatively, reductively, or using some combination of both types of bond scission. Oxidative bond scission with hydrogen peroxide, for example, results in the formation of sulfonic acid residues produced from cystine. The material produced using hydrogen peroxide for disulfide bond scission is highly ionic and has excellent water solubility. Reductive bond scission with mercaptoethanol, for example, results in the formation of cysteine residues produced from cystine. The material produced using this reductive technique is highly reactive and will readily re-crosslink.

Disulfide Bond Scission and Keratin Extraction

The proteins, preferably α-keratin, may be processed and/or isolated in any manner that renders them sufficiently soluble in the reaction media for crosslinking reaction(s) to occur. A number of the reactions described below call for an anhydrous solvent. Persons of ordinary skill in the art will recognize that anhydrous solvents include a large number of solvents, including, but not necessarily limited to 1,2,-dimethoxyethane, dimethylformamide, dimethylsulfoxide (DMSO), N-methyl pyrrolidone, and others. Generally, the reactions require the presence of at least some water.

Oxidation/Reduction of Cystine Residues

In a preferred embodiment, which uses keratin as a source material (e.g. human hair), the hair is oxidized by a suitable oxidizing agent. Suitable oxidizing agents include, but are not necessarily limited to hydrogen peroxide, peracetic acid, percarbonates, persulfates, chlorine dioxide, sodium and calcium peroxides, perborates, and hypochlorite. The oxidants are used at a concentration of up to about 35%, preferably at from about 0.1% to about 10%. The oxidation preferably occurs at reflux temperatures.

In a preferred embodiment, the hair is treated with hydrogen peroxide ($H_2O_2$), at from about 0.1% to about 10%, most preferably 1%, in order to disrupt the cuticle and swell the keratin source material. This process also converts some fraction of the cystine residues into sulfonic acid groups. The amount of oxidation may be controlled by varying the time of oxidation, preferably from about 0 hours to about 4 hours, while retaining the other conditions of the oxidation reaction constant. These conditions include concentration and type of oxidant, temperature, and ratio of extracting media to keratin source material. After the reaction is complete, the oxidized hair is filtered and rinsed, preferably with deionized water. The filtrate is discarded and the hair allowed to dry.

Where other conditions of oxidation are maintained constant, the conversion rate of cystine to sulfonic acid residues is roughly proportional to the amount of time used for the oxidation. Residual cystines in the resulting oxidized keratin solids are converted to other sulfur-containing moieties using reductive techniques. Preferably, the disulfide-bridged cystine group is converted to a thiol group, which has utility of it's own, or can be modified using a variety of chemical techniques.

Reaction with a Reducing Agent

If oxidized, the oxidized hair preferably is treated with a reducing agent. Treatment of oxidized keratin proteins with reducing agents facilitates the formation of cysteine from cystine, but tends to leave the previously oxidized groups unaltered. Suitable reducing agents include, but are not necessarily limited to thioglycolic acid and salts thereof, mercaptoethanol, dithiothreitol, thioglycerol, thiolactic acid, glutathione, cysteine, sodium sulfide, and sodium hydrosulfide. Preferred reducing agents are thioglycolic acid and mercaptoethanol, most preferably thioglycolic acid.

In order to treat the oxidized hair with the reducing agent, the previously oxidized hair is suspended in the reducing agent typically at a concentration of up to about 10N, preferably from about 0.1N and 1N; at a pH greater than about 7, preferably equal to or greater than 9, most preferably 9; a temperature of from about 25 to about 80° C., preferably about 60° C., preferably for a time period of from about 1 to about 72, most preferably about 24 hours. The reaction occurs under an inert atmosphere, preferably nitrogen. The liquid fraction is separated from any remaining solids using known means, including but not necessarily limited to filtration, or cannulation and/or centrifugation, preferably under inert atmosphere. A preferred method of separation is filtration. Once the solids are removed, the soluble keratin proteins are isolated from the solution by addition of a water-miscible non-solvent, or by spray drying. Water-miscible non-solvents include, but are not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The resulting keratin proteins are dried using known techniques, preferably overnight under vacuum at room temperature. This process results in the keratin having both sulfonic acid groups and thiol groups.

Thiols possess reactivities similar to alcohols, and can be used to perform a multitude of known organic chemical reactions, such as those described in McMurry, J., *Organic Chemistry*, Brooks/Cole Publishing Co., Monterey, Calif. (1984); Scudder, P. H., Electron Flow in Organic Chemistry, John Wiley & Sons, New York, N.Y. (1992); Stowell, J. C., *Intermediate Organic Chemistry*, John Wiley & Sons, New York, N.Y. (1994), incorporated herein by reference. The ratio of sulfonic acid to thiol is primarily controlled by the quantity of primary reactive sites remaining after oxidation. Of course, the rate of reduction will also be affected by reagent concentration(s), reaction temperature(s), and exposure time(s).

Reductive/Reductive Extraction

Reductive chemistries also are known for disulfide bond scission in keratin: See Wardell, J. L., "Preparation of Thiols" in *The Chemistry of the Thiol Group*, Patai, S. (Editor), pp. 163–353, John Wiley & Sons, New York, N.Y. (1974), incorporated herein by reference. HMWK's may be extracted from hair using at least two reductive extractions, as described in Crewther, W. G., Fraser, R. D. B., Lennox, F. G., and Lindley, H., "The Chemistry of Keratin" in *Advances in Protein Chemistry*, Anfinsen, C. B., Jr., Anson, M. L., Edsall, J. T., and Richards, F. M. (Editors), Academic Press, New York, pp. 191–346 (1965), incorporated herein by reference.

Suitable reducing agents include, but are not necessarily limited to thioglycolic acid and salts thereof, mercaptoethanol, dithiothreitol, thioglycerol, thiolactic acid, glutathione, cysteine, sodium sulfide, and sodium hydrosulfide. Preferred reducing agents are thioglycolic acid and mercaptoethanol, most preferably thioglycolic acid.

In order to selectively reduce and extract the desired proteins, the hair (or other protein source) is suspended in a reducing agent at a concentration of from about 0.1N to about 10N, preferably about 1.0N. Gentle swelling of hair fibers is achieved at a pH of about 9 or more, preferably at a pH of from about 9 to about 10.5. Hence, the initial reduction takes place at a temperature of from about 20 to about 100° C., preferably at about 25° C. The time period required to accomplish the first reduction is from about 4 to about 24 hours, most preferably about 12 hours. The reaction occurs under an inert atmosphere, preferably nitrogen. The liquid fraction is separated from remaining solids using known means, including but not necessarily limited to filtration, cannulation, and/or centrifugation, preferably under inert atmosphere. A preferred method of separation is filtration.

A second extraction is performed on the reduced solids using a suitable swelling agent, preferably urea, bases such as ammonium hydroxide, sodium hydroxide, or potassium hydroxide. A most preferred swelling agent for this second extraction is concentrated urea. The second extraction effectively removes the reduced fibrous α-keratin from inside the cuticle. The second extraction occurs at from about 1M to about 10M urea, preferably about 7M urea, for a period of at least about 1 hour, preferably from about 1 to about 72 hours, most preferably about 24 hours. The second extraction occurs at room temperature, but may take place at temperatures of from about 20° C. to about 100° C., preferably about 25° C. The liquid fraction is separated from the empty, intact cuticle, using known means. Suitable means include but are not necessarily limited to filtration, cannulation and/or centrifugation, preferably under inert atmosphere. A preferred method of separation is filtration.

Once the cuticle is removed, the extracted keratin proteins may be retained in solution for further use, or they may be isolated from the solution by addition to a water-miscible non-solvent, or by spray drying. Water-miscible non-solvents include, but are not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The precipitated proteins are dried using known techniques, preferably overnight under vacuum at room temperature. The dried keratin proteins are ground into a powder, sometimes referred to as "HMWK powder."

Silicone-Based Crosslinking Agents

In a most preferred embodiment, the crosslinking agent is a multifunctional silicone-based material. Silicones are a family of biocompatible materials that have been used in a myriad of medical applications. Silicone gel sheeting, a form of lightly crosslinked silicone polymer, promotes wound healing and lessens the degree of hypertrophic scar formation. The technology of silicone chemistry is varied and useful, particularly with respect to elastomer formation, as many crosslinking modalities have been developed. Thomas, D. R., "Cross-linking of Polydimethylsiloxanes", in *Siloxane Polymers*, Clarson, S. J. and Semlyen, J. A. (Editors), PTR Prentice Hall, New Jersey, pp. 567–615 (1993), incorporated herein by reference. Many of these crosslinking chemistries can be adapted for use in other systems such that copolymer and interpenetrating networks comprising at least some silicone have been produced. The beneficial wound healing attributes of silicone biomaterials, combined with their flexible chemistry, makes them ideal candidates for crosslinking keratin-based biomaterials.

Silicones are bioinert and resilient in biological systems. A bioinert crosslinking agent has the advantage of maintaining the biological stealth of the system of which it is a part. The combination of keratin with silicone-based crosslinking agents combines the wound healing efficacy of both biomaterials without compromising the inherent biocompatibility of keratin.

Suitable silicone cross-linking agents, or polysiloxanes, are molecules having recurring Si—O linkages:

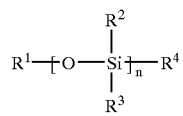

wherein n is from about 1 to about 50, and $R^1$, $R^2$, $R^3$, and $R^4$ can be a large variety of groups, wherein at least two of $R^1$, $R^2$, $R^3$, and $R^4$ comprise a "reactive functionality," defined as a functionality that is reactive toward reactive pendant groups on the protein molecules to be interlinked.

Suitable reactive functionalities comprise one or more reactive moieties selected from the group consisting of reactive unsaturated carbon-carbon bonds, reactive oxygens, reactive nitrogens, reactive sulfurs, and reactive halogens. Preferred reactive functionalities include, but are not necessarily limited to reactive unsaturated carbon-carbon bonds, hydrido groups, hydroxyl groups, alkylamine groups, alkylmercapto groups, alkoxy groups, trifluoroalkyl groups, wherein the alkyl moiety comprises from about 1 to about 6 carbon atoms. A preferred trifluoroalkyl group is a trifluoropropyl group; a preferred alkoxy group is an epoxy group, and a preferred unsaturated carbon-carbon bond is a vinyl group.

Examples of suitable $R^1$, $R^2$, $R^3$, and $R^4$ groups, some of which are reactive functionalities and some of which are not, include, but are not necessarily limited to hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise one or more heteroatoms selected from the group consisting of nitrogen, oxygen, and sulfur; cyclic, linear, and branched alkenyl and heteroalkenyl groups having from about 2 to about 6 carbon atoms, and mercapto functionalized versions thereof and resonance hybrids thereof, said groups comprising both unsubstituted groups and groups substituted with at least one reactive functionality; carboxyl groups and salts, esters, and amides thereof comprising cyclic, linear, and branched alkyl groups, heteroalkyl groups, alkenyl groups, and heteroalkenyl groups having from about 1 to about 6 carbon atoms wherein said hetero groups comprise one or more heteroatoms selected from the group consisting of nitrogen, oxygen, and sulfur; aromatic groups; alkanols and alkenols having from about 1 to about 6 carbon atoms; alkanolamides and alkenol amides having from about 1 to about 6 carbon atoms; and combinations thereof; alkoxy groups (sometimes referred to herein as "alkyl ethers") comprising one or more alkyl moieties having a total of from about 1 to about 6 carbon atoms, hydrido groups, and hydroxyl groups. Preferred heteroalkyl groups include, but are not necessarily limited to acetoxy groups, silane groups optionally comprising one or more alkyl substitutent having a total of from about 1 to about 6 carbon atoms, and combinations thereof. Preferred alkoxy groups include, but are not necessarily limited to epoxy groups.

Preferably, $R^1$ and $R^4$ are moieties comprising reactive functionalities which are adapted to react with complementary functional groups on the protein molecules to be interlinked, preferably α-keratin molecules. In a preferred embodiment, $R^1$ and $R^4$ independently are selected from the group consisting of hydrogen, linear, branched or cyclic alkyl groups having from about 1 to about 6 carbon atoms, alkenyl groups having from about 2 to about 6 carbon atoms, hydrido groups, alkoxy groups comprising one or more alkyl groups having a total of from about 1 to about 6 carbon atoms, hydroxy groups, alkylamine groups, alkylmercapto groups, acrylate groups, methacrylate groups, halo groups, acetoxy groups, and epoxy groups. In a more preferred embodiment, both $R^1$ and $R^4$ comprise a moiety selected from the group consisting of vinyl groups and epoxy groups. Most preferably, $R^1$ and $R^4$ comprise the same moiety selected from the group consisting of vinyl groups and epoxy groups; and In a preferred embodiment, $R^2$ and $R^3$ independently are selected from the group consisting of hydrogen, cycloalkyl groups, vinyl groups, hydrido groups, trifluoroalkyl groups, phenyl groups, alkyl groups, alkoxy groups, alkylmercapto groups, and alkylamine groups; provided that, when one of $R^2$ or $R^3$ is a vinyl group, the other of $R^2$ or $R^3$ is a group other than a hydrido group; and, when one of $R^2$ or $R^3$ is a hydrido group, the other of $R^2$ or $R^3$ is a group other than a vinyl group. In an even more preferred embodiment, $R^2$ and $R^3$ preferably are relatively inert groups. Most preferably at least one of $R^2$ and $R^3$ is an alkyl group, more preferably a methyl group.

Commercially available silicone products include, but are not necessarily limited to vinyl functional, alkoxy functional (preferably epoxy functional), alkylamine functional, hydroxyl functional, and alkylmercapto functional polysiloxy polymers and copolymers, which are available, for example, from Gelest, Inc., Tullytown, Pa., or may be made using known methods, such as those described in Thomas, D. R., "Cross-linking of Polydimethylsiloxanes", in *Siloxane Polymers*, Clarson, S. J. and Semlyen, J. A. (Editors), PTR Prentice Hall, New Jersey, pp. 567–615 (1993), incorporated herein by reference. Most preferred commercially available vinyl functional products are generally available in molecular weights ranging from about 363 to about 5,500, with preferred molecular weights being from about 500 to about 3500.

A preferred crosslinking agent is the epoxycyclohexyl copolymer discussed in more detail below. More preferred is epoxypropoxypropyl-terminated silicones discussed in more detail below. Most preferred crosslinking agents are vinyl-terminated silicones. These crosslinking agents may be obtained, for example from Gelest, Inc., Tullytown, Pa., or prepared using known procedures.

(Epoxycyclohexylethyl)methylsiloxane-dimethylsiloxane copolymer generally is available in molecular weights ranging from 500 to 50,000, with preferred molecular weights being from about 650 to about 3500. (Epoxycyclohexylethyl)methylsiloxane-dimethyl siloxane copolymer has the following general structure:

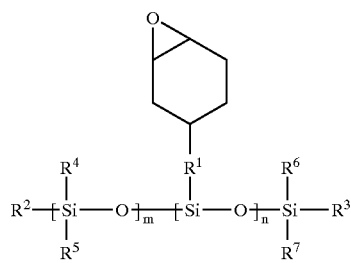

wherein m and n add to a total of from about 5 to about 50; $R^2$ and $R^3$ may be any of the groups listed as end groups $R^1$ and $R^4$ in the general formula for the silicone cross-linking agents given at the beginning of this section, and $R^1$, and $R^4$–$R^7$ may be any of the substitutents listed as the Si-substitutents $R^2$ and $R^3$ in the general formula for the silicone cross-linking agents given at the beginning of this section. Preferably, $R^1$ and $R^4$–$R^7$ are selected from the group consisting of alkyl groups having from about 1 to about 6 carbon atoms. $R^1$ preferably is a methyl group; $R^4$–$R^7$ preferably are methyl groups. A preferred (epoxycyclohexylethyl)methylsiloxane-dimethylsiloxane copolymer, which is commercially available from Gelest, has the following general structure:

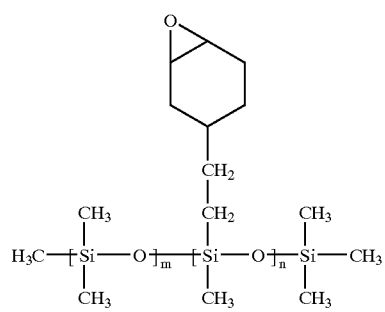

Preferred silicone-based crosslinking agents react with reactive groups on the protein molecules to produce biocompatible byproducts, preferably hydrogen, water, carbon dioxide, and/or any other biocompatible byproduct that is readily metabolized or excreted, removed from the network, or at least is not toxic to the human body. Suitable silicone-based crosslinking agents have either two or more of the same reactive functionalities, or two or more different reactive functionalities. Preferred silicone-based crosslinking agents have two or more of the same functional group.

Network Formation

Thiols and other chemical moieties contained in amino acid residues have utility as labile sites for crosslinking reactions to form protein networks, preferably networks having the properties of an elastomeric film. Preferred networks are made using HMWK proteins.

Once the desired crosslinking agent(s) are determined, proteins, preferably HMWK proteins, are dissolved in a suitable solvent. For most reactions, a preferred solvent is an aqueous solvent. In the case of silicone-based crosslinking agents, a preferred solvent is an anhydrous solvent comprising a base. Preferably, about 2 g of HMWK powder is mixed in the solvent containing a suitable base, and the mixture is stirred and heated to a temperature effective to dissolve the keratin, typically not more than 60° C. The pH of the solution is maintained at about 9 to 11 using a suitable base. Suitable bases include, but are not necessarily limited to ammonium hydroxide, sodium hydroxide, and potassium hydroxide, preferably ammonium hydroxide. At least about 5 wt. %, preferably about 10 wt. %, relative to the keratin, of a multifunctional crosslinking agent is added to the mixture, forming a network precursor solution. Depending upon the crosslinking agent, a catalyst or promoter may be added. The network precursor solution is distributed over an appropriate surface or mold, preferably to a thickness of from about 1 to about 10 mm, and cured by exposure to suitable energy, such as a heat lamp, an autoclave, a microwave, or a UV lamp. In a preferred embodiment for making films comprising a silicone-based crosslinking agent, the solutions are irradiated for a period of from about 1 hours to about 8 hours, preferably about 2 hours under a UV lamp ($\lambda$=365 nm) and then dried under a heat lamp effective to produce a temperature of at least about 60° C. for a period of from about 30 minutes to about 300 minutes, preferably about 4 hours.

Alternately, the keratin is dissolved in water and the silicone is dissolved in a separate solution of water-miscible organic solvent. Suitable organic solvents include ethanol, methanol, isopropyl alcohol, acetone, tetrahydrofuran, and dimethylsulfoxide. The two solutions are then mixed and a film cast from the resulting mixture.

Crosslinking Reactions

Crosslinking of the proteins and network formation occurs, generally, when a silicone-based crosslinking agent which is at least difunctional, or has at least two reactive groups, is used to crosslink between reactive pendant groups on two different keratin molecules. The silicone based reactant creates a bridge between keratin molecules, or an interprotein cross-link, and thus produces a three-dimensional network.

Proteins comprise amino acids, which generally have the formula:

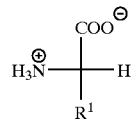

Table 1 summarizes the amino acid residues found in human hair, for example, and shows the "$R^1$" groups associated with each residue.

TABLE 1

Ranked average amounts of amino acids in human hair

| Amino Acid | $R^1$ Group | Nature | pKa | Iso-electric Point (pH) | Percent Composition in Hair |
|---|---|---|---|---|---|
| Cysteine | H—S—CH$_2$— | Nonpolar | 8.4 | 5.02 | 17.3 |
| Glutamic Acid | HO—C(=O)—CH$_2$—CH$_2$— | Polar | 4.5 | 3.22 | 13.9 |
| Arginine | NH$_2$—C(=NH)—N(H)—(CH$_2$)$_3$— | Polar | 12.5 | 11.15 | 9.85 |
| Serine | HO—CH$_2$— | Polar | None | 5.68 | 9 |
| Threonine | CH$_3$—CH(OH)— | Polar | None | 5.64 | 7.75 |
| Leucine | (CH$_3$)$_2$CH—CH$_2$— | Hydrophobic | None | 5.98 | 7.35 |
| Proline | (cyclic CH$_2$-CH$_2$-CH$_2$-) | Hydrophobic | None | 6.3 | 6.95 |
| Aspartic Acid | HO—C(=O)—CH$_2$— | Polar | 4.5 | 2.77 | 5.8 |
| Valine | (CH$_3$)$_2$CH— | Hydrophobic | None | 5.96 | 5.7 |
| Isoleucine | CH$_3$—CH$_2$—CH(CH$_3$)— | Hydrophobic | None | 5.94 | 4.75 |
| Glycine | H— | Nonpolar | None | 5.65 | 4.15 |
| Phenylalanine | C$_6$H$_5$—CH$_2$— | Hydrophobic | None | 5.48 | 3 |
| Alanine | CH$_3$— | Hydrophobic | None | 6 | 2.8 |
| Tyrosine | HO—C$_6$H$_4$—CH$_2$— | Hydrophobic | None | 5.66 | 2.6 |

TABLE 1-continued

Ranked average amounts of amino acids in human hair

| Amino Acid | $R^1$ Group | Nature | pKa | Iso-electric Point (pH) | Percent Composition in Hair |
|---|---|---|---|---|---|
| Lysine | $NH_2-(CH_2)_4-$ | Polar | 10.4 | 9.59 | 2.5 |
| Histidine | (imidazole-CH₂–) | Aromatic | 6.2 | 7.47 | 0.9 |
| Methionine | $CH_3-S-CH_2-CH_2-$ | Hydrophobic | None | 5.74 | 0.85 |
| Tryptophan | (indole-CH₂–) | Hydrophobic | None | 5.89 | 0.85 |

The most abundant amino acid in human hair is cysteine, which is found in the form of disulfide-bridged cystine groups. As discussed above, this group can be converted to other sulfur containing moieties, most notably thiol. Thiols theoretically can be reacted with reactive ends of a crosslinking agent using a number of chemical techniques, such as those described in S. Patai (Ed.), *the Chemistry of the Thiol Group*, Parts 1 and 2, John Wiley & Sons, New York, N.Y. (1974), incorporated herein by reference. Other reaction scenarios, such as those directed toward polymer synthesis, also are useful to convert thiol groups and other pendant groups to an assortment of desirable functional residues, including those described in Rempp, P. and Merrill, E. W., *Polymer Synthesis*, Huethig & Wepf Verlag Basel, Heidelberg, Germany (1986); Young, R. J. and Lovell, P. A., *Introduction to Polymers*, Chapman & Hall, London (1991); Odian, G., *Principles of Polymerization*, John Wiley & Sons, New York, N.Y. (1991), incorporated herein by reference.

In addition to cysteine, the following amino acids have pendant groups comprising nitrogen or oxygen which may be useful as reactive pendant groups; arginine, serine, glutamic acid, threonine, aspartic acid, lysine, asparagine, glutamine, tyrosine, tryptophan, and histidine. Where the protein is α-keratin, preferred amino acid residues comprising reactive pendant groups for crosslinking are cysteine, arginine, serine, and glutamic acid, most preferably cysteine and arginine.

The silicone-based crosslinking agents comprise at least two reactive functionalities. For convenience, the crosslinking agents described herein sometimes are referred to as "di-" functional. However, unless a crosslinking agent is expressly claimed or expressly stated to be di-functional only, it is to be understood that the crosslinking agents described herein may also be multi-functional, e.g., di-, tri, tetra-, etc.

Without limiting the invention to a particular theory or mechanism of action, unless expressly claimed, the following are crosslinking chemistries involved in producing the heterogeneous crosslinked protein networks:

Production of Thioether

A preferred reductive modification is the formation of a thiolate anion, followed by nucleophilic substitution employing an appropriate leaving group, yielding a thioether, preferably an alkoxy functional thioether (or a thioester). A preferred alkoxy functional thioether is an epoxy-functional thioether. The general reaction is shown below:

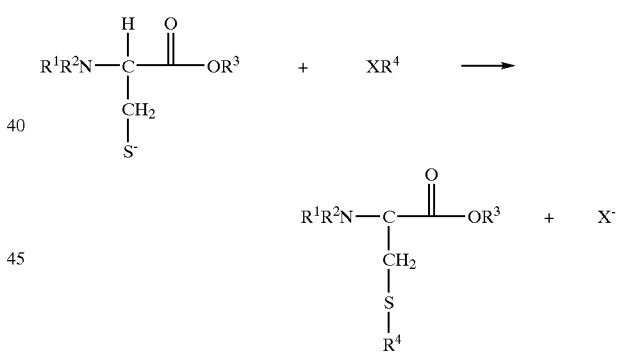

wherein $R^1$ and $R^2$ comprise entities selected from the group consisting of hydrogen and the remainder of the N-terminal portion of the protein molecule; $R^3$ comprises the remainder of the carboxy-terminal portion of the protein molecule; and, $R^4$ is a group adapted to form a thioether, preferably an alkoxy functional thioether. Suitable $R^4$ groups comprise a "substitution end," which bonds with the sulfur and a "reactive end" which reacts with the crosslinking agent. Suitable substitution ends include, but are not necessarily limited to unsubstituted and halo-substituted alkyl groups and alkylene groups having from about 1 to about 8 carbon atoms, including resonance hybrids, such as allyl groups, and unsubstituted and halo-substituted aryl groups. Suitable reactive ends include, but are not necessarily limited to acyl groups, and polyalkylethers containing from about 1 to 50 repeat groups, silane groups, and silicone groups. Preferred reactive ends include, but are not necessarily limited to carboxyl groups, hydroxyl groups, and alkoxide groups. A most preferred reactive end is an epoxide group. In the foregoing formula, X may be any appropriate leaving group. Suitable leaving groups include, but are not necessarily limited to halide groups, tosylate groups, acetate groups, hydroxyl groups, alkoxy groups, and amine groups. Preferred X groups are halides, most preferably chlorine. In a most preferred embodiment, $XR^4$ is epichlorohydrin.

The thiolate anion can be generated from thiol, or more directly from the water soluble protein feedstock, preferably a keratin feedstock, by reaction with a reactive nucleophile. Suitable nucleophiles include alkyl and aryl functional sulfide salts, sulfonates, isocyanates, thiocyanates, halides, hydrosulfide, hydroxide, alkoxides, azides, and acetates preferably alkyl and aryl sulfide salts, hydrosulfide, hydroxide, alkoxides, azides, and acetates. A most preferred nucleophile is sodium sulfide.

The reaction where RX is epichlorohydrin is shown below:

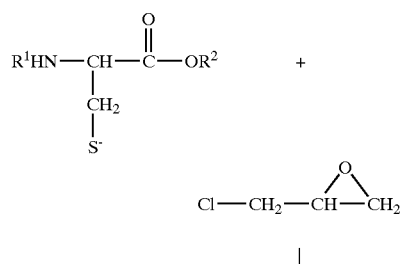

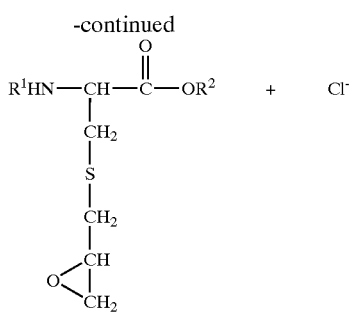

wherein $R^1$ and $R^2$ are the remainder of the water soluble protein molecule of which cysteine is a part.

In order to form the foregoing epoxide functionalized water soluble proteins, preferably water soluble keratin, a water soluble keratin source material is first produced, preferably as described above. The water soluble keratin are then exposed to a solution of "RX", preferably epichlorohydrin, in aqueous solution at a pH of from about 9 to about 11. The RX is typically at a concentration of up to about 20 mole percent relative to keratin, preferably from about 5 to 10 mole percent relative to keratin, most preferably about 10 mole. %. The pH is greater than about 7, preferably greater than about 9. The temperature is from about 20 to about 100° C., preferably about 60° C. The reaction continues for a time period of from about 1 to about 72 hours, most preferably about 24 hours. The result is epoxidized thiol groups.

In a most preferred embodiment, the epoxidized keratin are cured into an elastomer using multifunctional silicone-based crosslinking agents, such as amine-functional silicones, which are available from Gelest, Inc. (Tullytown, Pa.). The reaction is as follows:

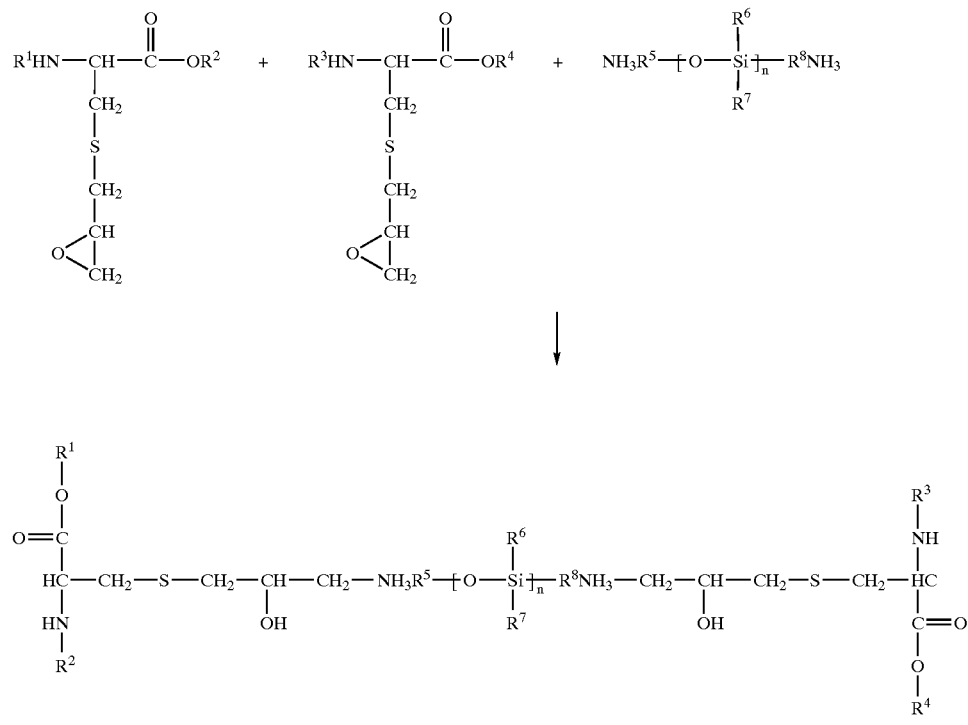

Peptide A    Peptide B wherein $R^1$ and $R^2$ are the remainder of the water soluble protein "A" bearing an epoxy functionalized cysteine; $R^3$ and $R^4$ are the remainder of the water soluble protein molecule B bearing an epoxy functionalized cysteine; $R^5$ and $R^8$ preferably are alkyl groups having from about 1 to about 6 carbon atoms, most preferably n-propylene groups; and $R^6$ and $R^7$ independently are selected from the groups described above in the general formula for the silicone cross-linking agents, specifically $R^2$ and $R^3$ thereof. Most preferably $R^6$ and $R^7$ are relatively inert groups, such as methyl groups. Although it is theoretically possible for water soluble protein molecule A and B to be the same molecule, it is preferred for proteins A and B to be different molecules in all of the embodiments described herein, preferably different water soluble α-keratin molecules.

In order to perform this reaction, the keratin are dissolved in water and the silicone is dissolved in a separate water-miscible organic solvent. Suitable organic solvents include ethanol, methanol, isopropyl alcohol, acetone, tetrahydrofuran, and dimethylsulfoxide. The two solutions are mixed, along with an appropriate catalyst if needed, and the mixture is cast into a film. Film drying can be accomplished by air drying, or accelerated by the application of heat or vacuum. The curing is accomplished by exposure to a source of energy, preferably heat, irradiation, or a combination thereof.

Free Radical Addition to Reactive Pendant Groups

Addition reactions such as free radical addition to an unsaturated hydrocarbon represent another potential avenue to transformation of the thiol group. A variety of vinyl-functional silicones, for example, can be used to modify the thiol in the presence of an appropriate catalyst. Free radical catalysts can be initiated by heat or electromagnetic energy. The reaction scenario is shown below:

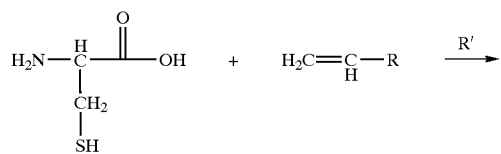

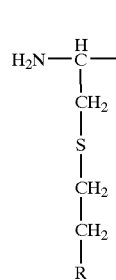

When the thiol is attached to a molecule of keratin, and if the R group of the allyl derivative is a silicone, a keratin-silicone copolymer is formed. If the silicone is at least difunctional (e.g. vinyl-terminated polydimethylsiloxane), a network or elastomeric structure results.

In order to perform this reaction, a suitable amount of keratin powder is dissolved in an anhydrous solvent, preferably comprising a suitable base. A vinyl terminated silicone fluid is added after complete dissolution, along with a suitable quantity of a free radical initiator, preferably anthraquinone-2-sulfonic acid sodium salt monohydrate. (Aldrich, Milwaukee, Wis.). Other suitable free radical initiators include, but are not necessarily limited to free radical photoinitiators including, but not necessarily limited to benzoin ethers, benzil ketals, α-dialkoxyacetophenones, α-hydroxyalkylphenones, α-aminoalkylphenones, acylphosphine oxides, benzophenone/amines, thioxanthones/amines, titanoocenes, and certain silanes. The amount of the vinyl functional silicone fluid added is from about 1 to about 20 weight percent relative to the amount of keratin used, preferably about 10 weight percent. The viscous solution is cast onto a suitable mold. For laboratory purposes, a suitable mold is a Teflon™ coated petri dish. The viscous solution is cured for a time effective to produce an elastomeric film having desired properties. The curing is accomplished by exposure to a source of energy, preferably heat, irradiation, or a combination thereof. In a preferred embodiment, the viscous fluid is irradiated for a period of from about 1 hour to about 4 hours, preferably about 2 hours under a UV lamp (λ=365 nm) and then dried under a heat lamp effective to produce a temperature of at least about 60° C. for a period of from about 30 minutes to about 300 minutes, preferably about 4 hours.

Conversion of Thiol by Condensation

Condensation reactions such as transesterification, for example, can be used to generate thioesters of a silicone-based crosslinking agent. An example of a transesterification reaction is shown in Scheme 3.

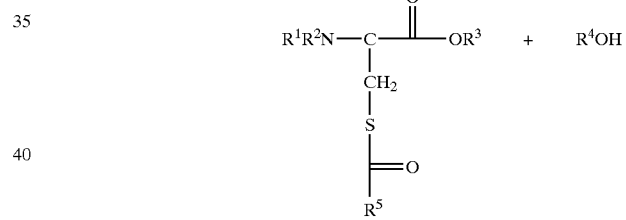

wherein $R^1$ and $R^2$ comprise entities selected from the group consisting of hydrogen and the remainder of the N-terminal portion of the protein molecule; $R^3$ comprises the remainder of the carboxy-terminal portion of the protein molecule; $R^4$ is an appropriate leaving group; and, $R^5$ comprises a silicone-based entity. Suitable $R^4$ groups include, but are not necessarily limited to hydrogen, alkyl groups having from about 1 to 6 carbon atoms, and aryl groups, including benzyl groups. $R^5$ also may comprises silicone groups.

Where $R^5$ is a silicone group, that group preferably has the following general structure:

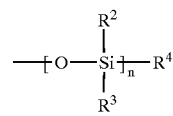

wherein n, $R^2$, $R^3$, and $R^4$ are the same as the corresponding groups described above in the general formula for the silicone cross-linking agents.

Where $R^5$ comprises a silicone-based entity, the following is an exemplary reaction:

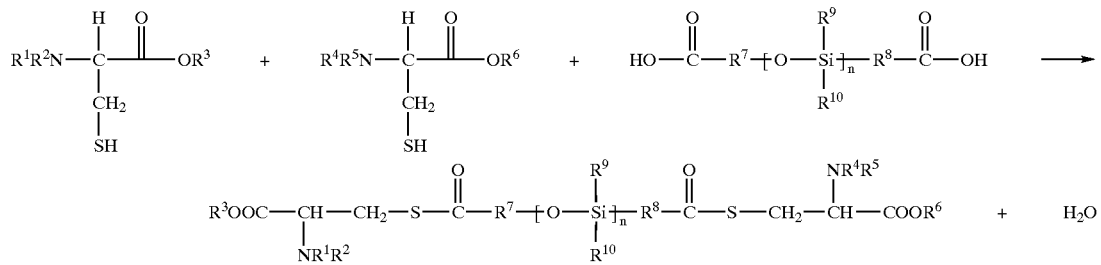

wherein n is from about 1 to about 50; $R^1$, $R^2$, and $R^3$ are the remainder of a first water soluble protein molecule; $R^4$, $R^5$, and $R^6$ are the remainder of a second water soluble protein molecule; $R^7$ and $R^8$ preferably are selected from the group consisting of alkyl groups having from about 1 to about 6 carbon atoms, alkoxy groups comprising one or more alkyl groups having a total of from about 1 to about 6 carbon atoms, silyl groups having the same pendant substituents as the remainder of the polymer chain ($R^9$ and $R^{10}$), and combinations thereof; and $R^9$ and $R^{10}$ independently are selected from the groups described above in the general formula for suitable silicone cross-linking agents, specifically $R^2$ and $R^3$ thereof. Most preferably $R^2$ and $R^3$ are relatively inert groups, such as methyl groups.

In order to perform this reaction, the keratin are dissolved in water and the silicone is dissolved in a separate water-miscible organic solvent. Suitable organic solvents include ethanol, methanol, isopropyl alcohol, acetone, tetrahydrofuran, and dimethylsulfoxide. The two solutions are mixed, along with an appropriate catalyst if needed, and the mixture is cast into a film. Film drying can be accomplished by air drying, or accelerated by the application of heat or vacuum. The curing is accomplished by exposure to a source of energy, preferably heat, irradiation, or a combination thereof.

Addition of Amine Groups

Addition reactions between reactive amine groups and oxirane compounds occur readily without the aid of a catalyst. Preferred oxirane compounds are diepoxides having the following general structure:

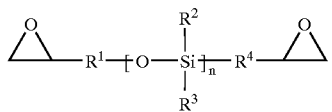

wherein n is from about 5 to about 50; $R^2$ and $R^3$ independently are selected from the groups described above in the general formula for suitable silicone crosslinking agents, specifically $R^2$ and $R^3$ thereof. Most preferably $R^2$ and $R^3$ are relatively inert groups, such as methyl groups; and, $R^1$ and $R^4$ are substantially any moieties which do not interfere with the desired characteristics of the film. Preferably, $R^1$ and $R^4$ are selected from the group consisting of alkyl groups having from about 1 to about 3 carbon atoms, alkoxy groups comprising one or more alkyl groups having a total of from about 1 to about 6 carbon atoms, and silane groups optionally comprising one or more alkyl substituents having from about 1 to about 6 carbon atoms, most preferably methyl groups, and combinations thereof.

More preferred oxiranes have the following general structure:

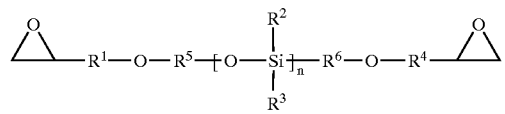

wherein n is from about 5 to about 50; $R^2$ and $R^3$ independently are selected from the groups described above with respect to the silicone-based crosslinking agent, specifically $R^2$ and $R^3$ thereof. Most preferably $R^2$ and $R^3$ are relatively inert groups, such as methyl groups; and, $R^1$ and $R^4$ are substantially any moieties which do not interfere with the desired characteristics of the film. Preferably, $R^1$ and $R^4$ are selected from the group consisting of alkyl groups having from about 1 to about 6 carbon atoms, preferably from about 1 to about 3 carbon atoms. $R^5$ and $R^6$ are selected from the group consisting of alkyl groups having from about 1 to about 6 carbon atoms, preferably from about 1 to about 3 carbon atoms, silane groups optionally comprising one or more alkyl substituents having from about 1 to about 6 carbon atoms, most preferably one or more methyl substitutents, and combinations thereof.

A most preferred oxirane compound is epoxypropoxypropyl-terminated poly(dimethylsiloxane), available from Gelest, Inc., Tullytown, Pa., having the structure shown below:

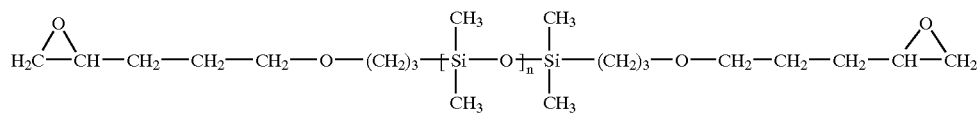

The crosslinking reaction of a diepoxy-silicone based crosslinker with arginine is as follows:

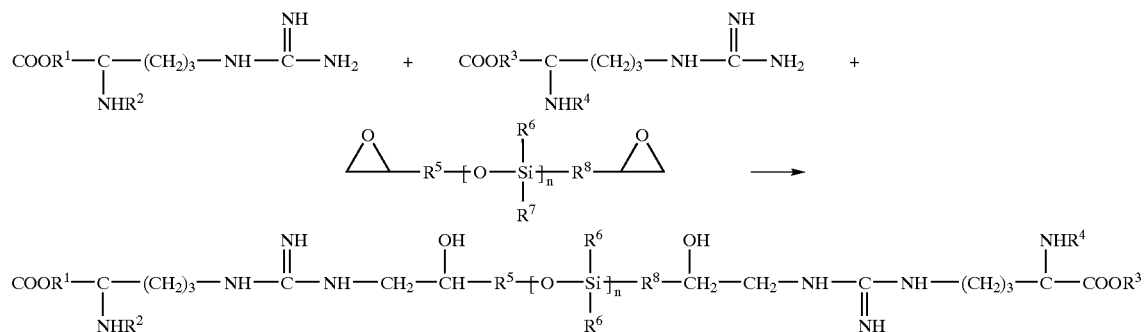

wherein $R^1$ and $R^2$ represent the remainder of one protein molecule; $R^3$ and $R^4$ represent the remainder of a separate protein molecule, preferably different α-keratin molecules;

In order to perform this reaction, solubilized keratin are exposed to a solution containing an oxirane-terminated silicones, such as those available from Gelest, Inc., Tullytown, Pa., typically at a concentration of up to about 20 mole percent relative to keratin, preferably between 5 and 10 mole percent relative to keratin; at a pH greater than 7, preferably greater than 9, or less than 7, preferably less than 6; at a temperature of from about 0 to about 100° C., preferably about 30° C., preferably for a time period of from about 0 to about 72 hours, most preferably about 24 hours.

A similar reaction occurs when a diepoxide reacts with cysteine residues:

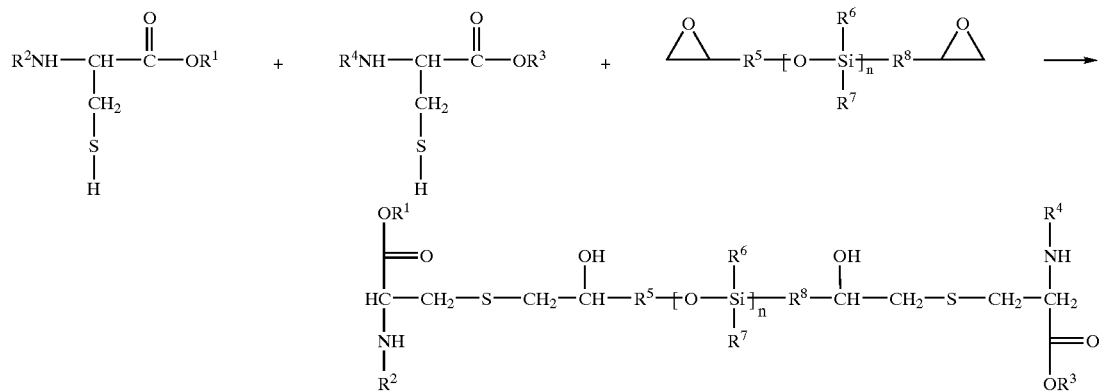

wherein $R^1$ and $R^2$ are the remainder of a first protein molecule and $R^3$ and $R^4$ are the remainder of a second protein molecule, preferably different α-keratin molecules. $R^5$ and $R^8$ are the corresponding moieties just described with respect to the reaction with arginine.

Persons of ordinary skill in the art will recognize that many of the crosslinking agents described herein will react with a variety of amino acid residues having pendant groups comprising a reactive nitrogen atom, sulfur atom, or oxygen atom. Hence, one end of a diepoxide may react with a cysteine residue while the other end of the diepoxide reacts with an arginine residue, as follows:

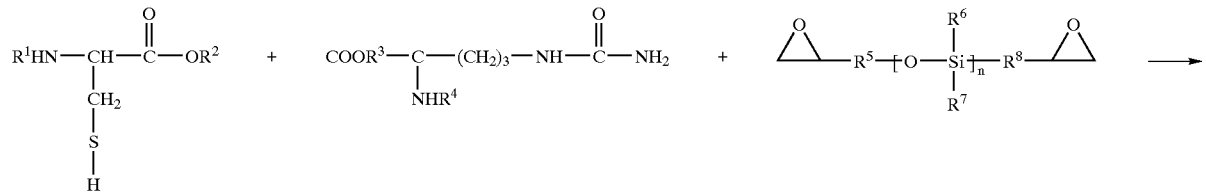

-continued

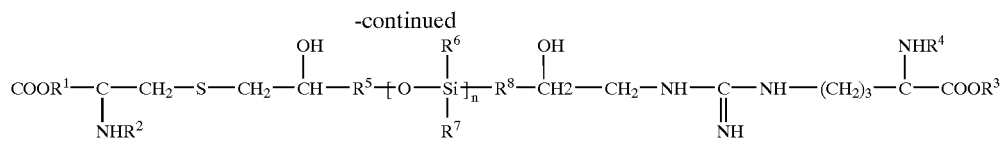

wherein $R^1$ and $R^2$ represent the remainder of one protein molecule; $R^3$ and $R^4$ represent the remainder of a separate protein molecule, preferably different α-keratin molecules; $R^5$ and $R^8$ may be any moiety which does not interfere with the desired characteristics of the film. Preferably, $R^5$ and $R^8$ are selected from the group consisting of propoxypropyl groups and alkyl groups having from about 1 to about 6 carbon atoms, more preferably from about 1 to about 3 carbon atoms; and $R^6$ and $R^7$ independently are selected from the groups described above with respect to the silicone crosslinking agents, specifically $R^2$ and $R^3$ thereof. Most preferably $R^6$ and $R^7$ are relatively inert groups, such as methyl groups.

The identity of amino acid residues linked by the crosslinking agent is not as important as the requirement that a sufficient quantity of crosslinking between protein molecules occurs to produce a film having desired properties. In a preferred embodiment, the crosslinking produces an elastomeric film.

Network Properties

As seen above, a three dimensional keratin-based network can be formed using a variety of chemistries. Preferably, the "dissolution rate" of such a network is controllable by controlling the crosslink density of the film and the level and type of functionality, particularly the functionality adjacent to the crosslink site. For example, the use of a crosslinking agent having one of the following characteristics reduces the dissolution rate of the resulting network: a crosslinking agent which forms S—C bonds, as opposed to more hydrolyzable bonds, such as ester bonds; a crosslinking agent which introduces substantial steric hindrance at the crosslink site; a crosslinking agent which is hydrophobic. The "dissolution rate" of the resulting network or film is measured by determining how long the film resists hydrolysis upon exposure to an aqueous buffer having a pH of about 7. A desirable "dissolution rate" will depend upon the application in which the film is to be used.

The invention will be better understood with reference to the following Examples, which are illustrative only:

EXAMPLE 1

500 g of clean, dry human hair was placed in a 12 L flask with 8.35 L of 1 w/v % $H_2O_2$ and brought to a gentle boil. The reaction was heated without stirring at reflux for 180 minutes. The hair was filtered, rinsed with deionized water and allowed to air dry.

100 g of oxidized hair was placed in a 2 L flask with 1 L of 1M thioglycolic acid solution adjusted to pH 9 with ammonium hydroxide. The reaction was heated to 60° C. under a nitrogen atmosphere with stirring for 24 hours.

The mixture of solids and liquid extract was poured into bottles under argon atmosphere. The bottles were sealed and centrifuged to affect separation of the solids. The liquid was cannulated into an 8-fold excess of cold ethanol, under nitrogen, and formed a precipitate. The precipitate was filtered, washed with ethanol, and dried under vacuum. The dried solids were ground to a powder using a mortar and pestle.

3 g of the keratin powder was dissolved into 15 mL of dimethysulfoxide (DMSO) with 1 mL of 30% ammonium hydroxide. After complete dissolution, 0.3 g of a vinyl-terminated silicone fluid (catalogue no. DMS-V03; Gelest, Inc., Tullytown, Pa.) and 0.1 g of anthraquinone-2-sulfonic acid sodium salt monohydrate (Aldrich, Milwaukee, Wis.) was added. The viscous solution was cast onto a Teflon™ coated petri dish and cured for 2 hours under a UV lamp (λ=365 nm). The film was further dried under a heat lamp for 4 hours. This process resulted in an elastomeric film of good quality.

EXAMPLE 2

175 g of clean dry hair was placed in a 4 L glass reactor with 3.5 L of 1M mercaptoethanol adjusted to pH 10.2 with potassium hydroxide. The solution was stirred under nitrogen for 21 hours, after which, the solids were separated by filtration. The reduced hair was then extracted with 2.3 of 7M aqueous urea solution at room temperature, under nitrogen, for 24 hours.

The reaction was centrifuged and the liquid filtered, then neutralized to pH 7 by addition of concentrated hydrochloric acid. The neutralized keratin solution was added dropwise to a 10-fold excess of ethanol to affect precipitation. The precipitate was filtered, rinsed with ethanol, and dried under vacuum. The dried solid was ground to a powder using a mortar and pestle.

5 g of the ground keratin powder was dissolved in 60 g of 30% ammonium hydroxide solution with the aid of stirring, sonication, and slight heating. After complete dissolution, the ammonium hydroxide was allowed to evaporate with the assistance of a dynamic nitrogen purge. To half of this solution was added 0.05 g of anthraquinone-2-sulfonic acid sodium salt monohydrate and a solution of 0.5 g of vinyl-terminated silicone (catalogue no. DMS-V03; Gelest, Inc., Tullytown, Pa.) in 2 g of isopropyl alcohol. After ca. 30 minutes of stirring, the thick solution was cast onto a Teflon coated petri dish and cured under a UV lamp for ca. 3 hours. The film was then dried under a heat lamp for ca. 1 hour. The film was placed in deionized water for 24 hours and did not dissolve.

Persons of ordinary skill in the art will recognize that many modifications may be made to the present invention without departing from the spirit and scope of the present invention. The embodiment herein is meant to be illustrative only and should not be taken as limiting the invention, which is defined in the claims.

I claim:

1. A method for making a keratin network crosslinked by a multi-functional crosslinking agent comprising silicone, said method comprising exposing a plurality of α-keratin molecules comprising reactive pendant groups to said crosslinking agent under conditions effective to form covalent interprotein crosslinks between first reactive functionalities on said crosslinking agent and first reactive pendant groups on a first group of said α-keratin molecules, said conditions also being effective to form covalent interproteincrosslinks between second reactive functionalities on said crosslinking agent and second reactive pendant groups on a second group of α-keratin molecules, wherein said crosslinking agent has the following general structure:

5. The network of claim 4 wherein said first reactive functionalities and said second reactive functionalities comprise the same reactive moiety.

6. A heterogeneous crosslinked network comprising the following crosslinks:

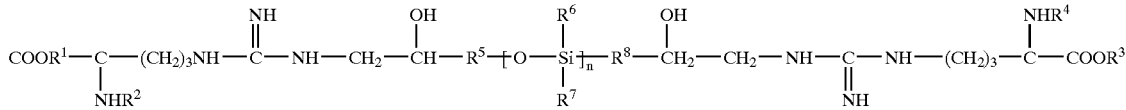

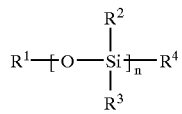

wherein n is from about 1 to about 50; and,
at least two of $R^1$, $R^2$, $R^3$, and $R^4$ comprise at least one reactive functionality; wherein $R^1$, $R^2$, $R^3$, and $R^4$ are selected from the group consisting of hydrogen; cyclic, linear, and branched alkyl and heteroalkyl groups having from about 1 to about 6 carbon atoms, said groups comprising both unsubstituted groups and groups substituted with one or more reactive functionalities, wherein said heteroalkyl groups comprise acetoxy groups, silane groups optionally comprising one or more alkyl substitutent having a total of from about 1 to about 6 carbon atoms, or combinations thereof.

2. The method of claim 1 wherein said first reactive functionality and said second reactive functionality comprise the same reactive moiety.

3. The method of claim 1 wherein $R^1$ and $R^4$ comprise said first and second reactive functionalities.

4. A network consisting essentially of keratin molecules comprising interkeratin crosslinks comprising first covalent bonds between first reactive functionalities on a plurality of molecules of a crosslinking agent comprising silicone and first reactive pendant groups on a plurality of first keratin molecules and second covalent bonds between second reactive functionalities on a plurality of molecules of said crosslinking agent and second reactive pendant groups on a plurality of second keratin molecules, wherein said crosslinking agent has the following general structure:

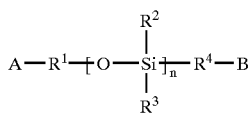

wherein n is from about 1 to about 50; and, A and B are the remainder of first and second protein molecules; at least two of $R^1$, $R^2$, $R^3$, and $R^4$ comprise at least one reactive functionality; wherein $R^1$, $R^2$, $R^3$, and $R^4$ are selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, or combinations thereof.

wherein $R^1$ and $R^2$ are a remainder of a first keratin protein molecule; $R^3$ and $R^4$ is a remainder of a second protein molecule; and, $R^5$, $R^6$, $R^7$, and $R^8$ are reacted groups selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

7. The network of claim 6 wherein at least one of $R^6$ and $R^7$ is an alkyl group.

8. The network of claim 6 wherein at least one of $R^6$ and $R^7$ is a methyl group.

9. The network of claim 6 wherein $R^5$ and $R^8$ comprise n-propoxypropyl groups.

10. The network of claim 7 wherein $R^5$ and $R^8$ comprise n-propoxypropyl groups.

11. A heterogeneous crosslinked network comprising the following crosslinks:

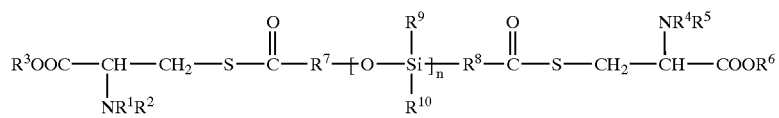

wherein $R^1$, $R^2$ and $R^3$ are a remainder of a first keratin protein molecule; $R^4$, $R^5$, and $R^6$ are a remainder of a second keratin protein molecule; and, $R^7$, $R^8$, $R^9$ and $R^{10}$ are selected from the group consisting of cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

12. The network of claim 11 wherein at least one of $R^9$ and $R^{10}$ is an alkyl group.

13. The network of claim 11 wherein $R^7$ and $R^8$ are selected from the group consisting of alkyl groups having from about 1 to about 6 carbon atoms and dimethylsiloxy groups.

14. The network of claim 12 wherein $R^7$ and $R^8$ are selected from the group consisting of alkyl groups having from about 1 to about 6 carbon atoms and dimethylsiloxy groups.

15. A heterogeneous crosslinked network comprising the following crosslinks:

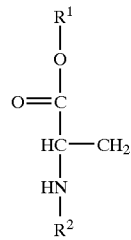 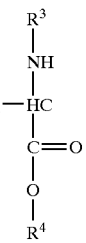

wherein $R^1$ and $R^2$ are a remainder of a first keratin protein molecule; $R^3$ and $R^4$ is a remainder of a second keratin protein molecule; and, $R^5$, $R^6$, $R^7$, and $R^8$ are reacted groups selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

16. The network of claim 15 wherein $R^5$ and $R^8$ comprise n-propoxypropyl groups.

17. A heterogeneous crosslinked network comprising the following crosslinks:

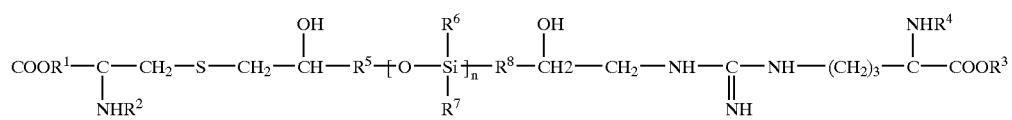

wherein $R^1$ and $R^2$ are a remainder of a first keratin protein molecule; $R^3$ and $R^4$ are a remainder of a second keratin protein molecule; and, $R^5$, $R^6$, $R^7$, and $R^8$ are reacted groups selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

18. The network of claim 17 wherein at least one of $R^6$ and $R^7$ is an alkyl group.

19. The network of claim 17 wherein $R^7$ and $R^8$ comprise n-propoxypropyl groups.

20. The network of claim 17 wherein said first and second protein molecules are keratin molecules.

21. A heterogeneous crosslinked network comprising the following crosslinks:

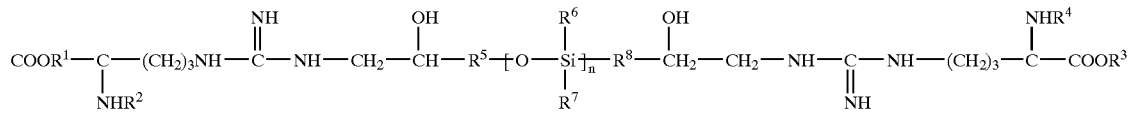

wherein $R^1$ and $R^2$ are a remainder of a first keratin protein molecule; $R^3$ and $R^4$ is a remainder of a second keratin protein molecule; and, $R^5$, $R^6$, $R^7$, and $R^8$ are reacted groups selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

22. The network of claim 21 wherein at least one of $R^6$ and $R^7$ is an alkyl group.

23. The network of claim 21 wherein at least one of $R^6$ and $R^7$ is a methyl group.

24. A heterogeneous crosslinked network comprising the following crosslinks:

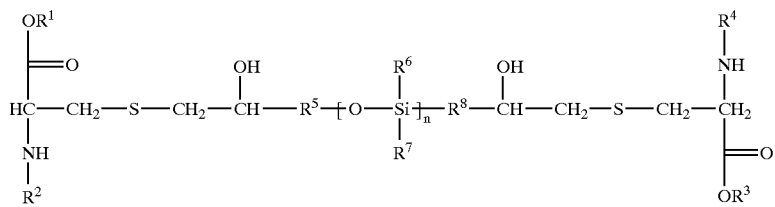

wherein $R^1$ and $R^2$ are a remainder of a first keratin protein molecule; $R^3$ and $R^4$ is a remainder of a second keratin protein molecule; and, $R^5$, $R^6$, $R^7$, and $R^8$ are reacted groups selected from the group consisting of hydrogen; cyclic, linear, and branched alkyl and heteroalkyl groups having from about 1 to about 6 carbon atoms, said groups comprising both unsubstituted groups and groups substituted with at least one reactive functionality, wherein said heteroalkyl groups comprise acetoxy groups, silane groups optionally comprising one or more alkyl substitutent having a total of from about 1 to about 6 carbon atoms, and combinations thereof.

25. The network of claim 24 wherein at least one of $R^6$ and $R^7$ is an alkyl group.

26. The network of claim 24 wherein at least one of $R^6$ and $R^7$ is a methyl group.

* * * * *

UNITED STATES PATENT AND TRADEMARK OFFICE
CERTIFICATE OF CORRECTION

PATENT NO. : 6,989,437 B2
DATED : January 24, 2006
INVENTOR(S) : Mark E. Van Dyke It is certified that error appears in the above-identified patent and that said Letters Patent is hereby corrected as shown below:

<u>Column 22,</u>
Lines 63-64, delete "interproteincrosslinks" and insert -- interprotein crosslinks --.

Signed and Sealed this

Twenty-eighth Day of March, 2006

JON W. DUDAS
*Director of the United States Patent and Trademark Office*